United States Patent
Wada et al.

(10) Patent No.: US 7,067,545 B1
(45) Date of Patent: Jun. 27, 2006

(54) REMEDIES FOR SPINOCEREBELLAR ATAXIA AND COMPOSITIONS FOR TREATING SPINOCEREBELLAR ATAXIA

(75) Inventors: Keiji Wada, Tokyo (JP); Toru Nishikawa, Tokyo (JP); Yasuyuki Ichimaru, Kanagawa (JP); Aiko Sawa, Kanagawa (JP); Toyakazu Hiranuma, Kanagawa (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 0 days.

(21) Appl. No.: 09/719,278

(22) PCT Filed: Jun. 3, 1999

(86) PCT No.: PCT/JP99/02971

§ 371 (c)(1),
(2), (4) Date: Feb. 8, 2001

(87) PCT Pub. No.: WO99/63989

PCT Pub. Date: Dec. 16, 1999

(30) Foreign Application Priority Data

Jun. 10, 1998 (JP) ................................ 10/161653

(51) Int. Cl.
*A61K 31/42* (2006.01)
*A61K 31/22* (2006.01)
*A61K 31/195* (2006.01)

(52) U.S. Cl. .................. 514/380; 514/551; 514/561
(58) Field of Classification Search .............. 514/380, 514/561, 551
See application file for complete search history.

(56) References Cited

U.S. PATENT DOCUMENTS 5,668,117 A * 9/1997 Shapiro .................... 514/55
5,848,043 A 12/1998 Takada et al.

FOREIGN PATENT DOCUMENTS

| EP | 0 319 824 A1 | 6/1989 |
| EP | 0 378 134 A2 | 7/1990 |
| EP | 0 844 607 | 5/1998 |
| EP | 0 867 868 | 9/1998 |

OTHER PUBLICATIONS

Contreras, Neuropharmacology, 29(3), 291–293, 1990, abstract.*
Biosis AN 1998: 514457 Saigoh et al, Brain Res., Oct. 12, 1998, 80(1), 42–27., abstract.*
Merck Index 10th edition, No. 7248, 1983.*
Sella C. et al., Database Inspec Online, XP002215396, 1981.
Saigoh et al. "The stereo–specific effect of D–serine ethylester and the D–cycloserine in ataxic mutant mice," *Brain Research* 808:42–47 (1998).
Vecsei et al., "Intracerebroventricular Injection of Kynurenic Acid, But Not Kynurenine, Induces Ataxia and Stereotyped Behavior in Rats," *Brain Research Bulletin* 25:623 (1990): abstract.
Database Acession No. XP002242838. Nakki, J Neurosci Res 1996 abstract.
Database Accession No. XP002242839. JP 19940169721, 1994 0721 abstract.
Database Accession No. XP008017772. Contreras 1989 abstract.

* cited by examiner

*Primary Examiner*—Rebecca Cook
(74) *Attorney, Agent, or Firm*—Peter F. Corless; John B. Alexander; Edwards Angell Palmer & Dodge LLP

(57) ABSTRACT

Remedies for spinocerebellar degeneration or compositions for treating the same which contain as the active ingredient one or more members selected from among D-cycloserine, D-serine esters, D-serine and salts thereof. A method for treating spincerebellar degeneration which comprises administering to a patient with this disease in an efficacious dose of one or more members selected from among D-cycloserine, D-serine esters, D-serine and salts thereof.

1 Claim, No Drawings

REMEDIES FOR SPINOCEREBELLAR ATAXIA AND COMPOSITIONS FOR TREATING SPINOCEREBELLAR ATAXIA

This is a 371 of PCT/JP99/02971 field Jun. 3, 1999.

Technical Field

The present invention relates to a remedy for treatment of spinocerebellar degeneration comprising D-cycloserine, D-serine or D-serine ester as an active ingredient, a composition for treatment of spinocerebellar degeneration comprising said remedy for treatment of spinocerebellar degeneration and pharmaceutically acceptable carrier thereof, and method for treatment thereof.

BACKGROUND ART

D-cycloserine is a known antituberculous antibiotic [Welch, H. et al. Antibiot. Med. & Clin. Therapy, 1(2), 72, 19551] and is used for administration of once 250 mg, b.i.d. per orally. D-cycloserine is known to show high bioavailability and long half-life as well as good transport into the brain (Nair, K. G. S. et al. Antibiot. Ann., 56, 136–140, 1955 and Mandell, C. L. and Petri, W. A. In Goodman and Gilman's The Pharmacological Basis of Therapeutics, 9th Ed. New York: McGraw-Hill, pp 1164–1165, 1996). It has also known that D-cycloserine selectively acts on the glycine binding site (strychnine-insensitive glycine binding site) of the NMDA (N-methyl-D-aspartate) receptor, which is one of the glutamate receptors, the glutamate is the one of the excitatory neurotransmitter, in the nervous system (Watson, G. B. et al. Brain Res., 510, 158–160, 1990 and Kemp, J. A. and Leeson, P. D. TiPS, 14, 20–25, 1993).

It has reported that D-cycloserine acts on the glycine binding site as a partial agonist to reveal various actions on the central nervous system [Baxter, M. G. and Lanthorn, T. H. CNS Drug Reviews, 1(1), 74–90, 1995]. Among them, treatment of schizophrenia (JP-A-2-225412) and treatment for improving memory disorder in head injury and Alzheimer's disease (WO 96/15787 and WO 96/15788) are known.

However, an improving action of D-cycloserine on the CNS motor (cerebellar) functional disorder has not been known.

Spinocerebellar degeneration develops major symptom of cerebellar or spinal ataxia and is a general name for the ill-defined neuro-degenerative disease having main lesion on the nucleus or neural tracts in cerebellum or spinal cord. Generally, falling develops slowly but is progressive and some disease type is hereditarily expressed. Cranial CT and MRI indicate frequently cerebellar or brain stem atrophy. Major symptom is cerebellar or posterior spinal ataxia, but depending on the disease types, sometimes develops vegetative symptom or spastic paraplegia as well as showing pyramidal or extrapyramidal symptoms. Consequently, the symptoms show multiplicity.

In Japan, the diagnostic criteria of spinocerebellar degeneration was revised by "ataxia" research group, M.H.W. in 1991, and 9 or 10 diseases were temporary mentioned as an individual disease.

A ratio of nonhereditary spinocerebellar degeneration to hereditary spinocerebellar degeneration in Japan is higher than that in Europe and in the U.S. Hereditary spinocerebellar degeneration is frequent in Europe. Nonhereditary spinocerebellar degeneration includes olivopontocerebellar atrophy, Shy-Drager syndrome, striato-nigral degeneration and late cortical cerebellar atrophy. The incidence of spinocerebellar degeneration in Japan is reported mostly olivopontocerebellar atrophy which accounts for the largest in 35%, late cortical cerebellar atrophy in 13%, Shy-Drager syndrome in 7% and striato-nigral degeneration in 1.5%. The ratio of male to female is almost 1:1, but that of male to female in Shy-Drager syndrome is 5:1 which shows prevalent in male. (New Clinic for SCD-Clinic of Spinocerebellar Degeneration—Ed. Itoyama, Yasuto, Shinko Medical Publishers, 1996).

The cerebellar cortex is constructed by three layers of molecular layer, Purkinje cell layer and granule cell layer, and is prevalent to amino acids [excitatory amino acid: glutamic acid (Glu) and inhibitory amino acid: γ-aminobutyric acid (GABA)] as the neurotransmitters. Biochemical changes of spinocerebellar degeneration is different depending on the disease types. In the typical disease type, for example, olivopontocerebellar atrophy, amino acid receptors such as γ-aminobutyric acid B receptor (GABA B receptor) and quisqualic acid receptor are decreased in the molecular layer; NMDA receptor is also decreased in the granule cell layer; and γ-aminobutyric acid A receptor (GABA A receptor) and benzodiazepine receptor are decreased in the granule cell layer and the molecular layer (Albin, R. L,. and Gilman, S. Brain Res., 522, 37–45, 1990). However, an efficacy of agonist for glycine binding site of NMDA receptor on this disease has not been examined.

It has been known that D-serine exists in the mammalian brain as an endogenous substance (Hashimoto, A. et al. J. Neurochem., 60, 783–786, 1993 and J. Neurochem., 61, 348–351, 1993) and D-serine binding site, which is insensitive to DCK (5,7-dichlorokynurenate) antagonist for glycine binding site of NMDA type glutamate receptor, exists in the rat brain, especially in the cerebellum at high concentration (Matoba, M. et al. J. Neurochem., 69, 399–405, 1997). The DCK- and strychnine-insensitive D-serine binding sites are thought to be a new candidate of the site of action for the endogenous D-serine.

As described hereinabove, cause of spinocerebellar degeneration is unknown, consequently the treatment therefor is performed mainly by symptomatic treatment. The drug for treatment of spinocerebellar degeneration approved at present, in Japan is only TRH (thyrotropin-releasing hormone) preparation, which is applied for ataxia, Protirelin tartrate (Mano, Y. et al., Acta Neurol. Scand., 73, 352–358, 1986 and JP-2556193). Since ataxic symptom was improved by an intraperitoneal administration of TRH in the rolling mouse Nagoya, application for treatment of spinocerebellar degeneration was initiated. The therapeutic effect was, however, not sufficient in the prolongation of effect and efficacy and developing adverse effect. Since large amount of administration of TRH preparation is necessary and the administration has to be performed by an injection, patients have to be imposed severe stress. Therefore, development of oral medicine with sufficient therapeutic effect, and slight adverse effect has been expected in the clinical field.

DISCLOSURE OF THE INVENTION

We have tried to diligent examination in order to achieve the above problem, and found that D-cycloserine, D-serine or D-serine ester showed specific improved effect on ataxic mice [i.e. improved effect on CNS motor (cerebellar) functional disorder], then completed the present invention.

The present invention relates to a remedy for spinocerebellar degeneration comprising one or more members selected from the group consisting of D-cycloserine, D-serine ester and D-serine or salt thereof.

The present invention further relates to a method for treating spinocerebellar degeneration comprising administering effective amount of one or more members selected from the group consisting of D-cycloserine, D-serine ester and D-serine or salt thereof to patient with spinocerebellar degeneration. The present invention further relates to use of one or more members selected from the group consisting of D-cycloserine, D-serine ester and D-serine or salt, thereof for production of the composition for treatment of spinocerebellar degeneration comprising the remedy for spinocerebellar degeneration or the remedy for spinocerebellar degeneration and pharmaceutically acceptable carrier thereof.

BEST MODE FOR CARRYING OUT THE INVENTION

D-cycloserine used in the present invention is a known antibiotic produced by Streptomyces such as *Streptomyces garyphalus* and *S. orchidaceus* (Kuehl, Jr. et al. J. Am. Chem. Soc., 77, 2344, 1955 and others) and is called as cycloserine, orientmycin, oxamycin (trade name) and seromycin. It has used as antituberculous agent of oral administration preparation from the 1950s. D-cycloserine used as an active ingredient in the present invention is not limited, if it is the pharmaceutical grade D-cycloserine.

D-serine used in the present invention is D-form optically active isomer of amino acid serine, one of hydroxyamino acid, and can be obtained by conventional optical resolution (enzymatic method or preferential crystallization) of racemate, DL-serine. This can be purified to pharmaceutically sufficient quality by known method. D-serine of the present invention can be converted, if necessary, to pharmaceutically acceptable salt, for example, inorganic salt such as sodium salt and potassium salt or organic salt such as organic amine salt.

D-serine of the present invention can be used in the form of pharmaceutically acceptable ester. The ester can be a pharmaceutically acceptable ester, which can be metabolized to free D-serine or salt thereof; for example alkyl ester consisting of $C_{1-20}$, preferably $C_{1-10}$, straight or branched alkyl ester such as methyl ester and ethyl ester, and phosphate ester. D-serine ester is commercially available and such the product on the market can be used. D-serine can also be produced by the conventionally known process such as esterification of D-serine.

Effective dose of D-cycloserine, D-serine ester or D-serine and salt thereof in the pharmaceutical preparation of the present invention is approximately 10–250 mg/kg, preferably 10–50 mg/kg, as calculated by D-cycloserine in animals which is determined from results of pharmacological examinations in ataxia model animals, and can be adjusted depending on the condition and symptom of patients.

Such the dose in the present invention, for example effective dose of D-cycloserine in the ataxia model animals such as 10 mg/kg or 50 mg/kg (intraperitoneal administration) is demonstrated to be sufficiently low dose as compared with the known effective dose of D-cycloserine in the antituberculous agent (Iseman, M. D., N. Engl. J. Med. 329, 784–791, 1993). Since D-cycloserine is a partial agonist to the glycine binding site of NMDA receptor, it is known to show different central actions between low dose and high dose. The fact that improved action on ataxia is observed in the dose dependent manner at below 50 mg/kg (i.p.) in mice in the results of pharmacological examination hereinbelow, indicates agonistic action within said dose level. The said dose level in mice corresponds to the low dose of D-cycloserine reported by Baxter et al. [Baxter, M. G. and Lanthorn, T. H. CNS Drug Reviews, 1(1), 74–90, 1995, supra], as a result, effective dose in human can be estimated to be a low dose level.

Consequently, dose level in spinocerebellar degeneration of the present invention can possibly be set to below 1.00 mg/man/day and can be expected to be lower than the dose level of antituberculous agent of 250 mg/man/day. This means that, in the remedy for spinocerebellar degeneration, incidence of side effect is expected to be sufficiently low as compared with that of the conventional antituberculous agent.

Acute toxicity of D-cycloserine in mice is shown in Table 1 and is known to be high safety (Anderson, R. C. et al. Antibiotics and Chemotherapy, 6(5), 360–368, 1956).

TABLE 1

| Acute toxicity of cycloserine | |
|---|---|
| Administration Route | $LD_{50}$ (mg/kg) |
| Intravenous | approx. 1,800 |
| Intraperitoneal | approx. 2,900 |
| Subcutaneous | approx. 2,800 |
| Oral | approx. 5,300 |

A composition for treatment of spinocerebellar degeneration of the present invention is comprised of containing one or more members selected from the group consisting of the above D-cycloserine, D-serine ester and D-serine or salts thereof as a remedy for spinocerebellar degeneration, and can be administered orally or parenterally (for example, intravenous, intramuscular, subcutaneous, rectal and percutaneous administrations) to human or animals other than human. Consequently, the composition for treatment of spinocerebellar degeneration comprising remedy for spinocerebellar degeneration as the active ingredient can be prepared for suitable formulations depending on the route of administration.

Examples of oral preparations are tablet, capsule, powder, granule and syrup. Examples of parenteral preparation are injection for intravenous or intramuscular administration, rectal preparation, oily suppository and aqueous suppository. These formulations can be prepared by conventional means using excipients, disintegrators, binders, lubricants and coloring agents.

Examples of excipients are, for example, glucose, corn starch, sorbit and crystalline cellulose. Examples of disintegrators are, for example, starch, sodium alginate, gelatin powder, calcium carbonate, potassium citrate and dextran. Examples of binders are, for example, dimethyl cellulose, polyvinyl alcohol, polyvinyl ether, methyl cellulose, ethyl cellulose, gum arabic, gelatin, hydroxypropyl cellulose and polyvinyl pyrroridone. Examples of lubricants are talc, magnesium stearate, polyethylene glycol and hardened vegetable oil. The above formulations for injection can be prepared with adding, if necessary, buffer, pH adjuster and stabilizing agents.

The composition for treatment of spinocerebellar degeneration can be formulated by the method for conventional formulations using the above components.

An example of oral preparation of the composition for treatment of spinocerebellar degeneration of the present invention is a capsule containing D-cycloserine 250 mg as an active ingredient (components containing sodium lauryl sulfate, Red No. 3 and Blue No. 1).

Content of D-cycloserine, D-serine or D-serine ester in the composition for treatment of spinocerebellar degeneration of the present invention is different depending on the formulation, and is usually 0.1–50% by weight, preferably 0.1–20% by weight, in the total weight of the composition. Dose level can be determined preferably depending on each case by considering age, body weight and sex difference, diseases and degree of symptom of patients, and route of administration, and is generally 1–1000 mg/adult man/day, preferably 1–300 mg/adult man/day, which is administered once a day or separately for several times.

EXAMPLES

The present invention is explained in details but is not limited within these examples.

Example 1

Effect on Drug Induced Ataxia Mice
(Experimental Method)

Ataxia mice prepared by repeated administration of cytosine arabinoside 50 mg/kg into male mice, 1, 2 and 3-day old, respectively, were used at 6–7-week old in the experiments (Simada, M. et al. Arch. Neurol., 32, 555–559, 1975 and Matsui, K. et al. Exp. Anim., 32, 13–19, 1983). This model mouse is known to express ataxia caused by cerebellar neuro-degeneration detected as pathologically decreased numbers of cerebellar granule cells.

Improving effects of drugs on ataxia were evaluated according to the methods of Yamamoto et al. (Yamamoto and Shimizu, Eur. J. Pharmacol. 1.66, 295–297, 1989) and Matsui et al. (Matsui et al. Eur. J. Pharmacol., 254, 295–297, 1994; Neurosci. Lett., 212, 115–118, 1996) as follows.

The open-field apparatus with a 70 cm square filed surrounded by a 15 cm high wall was used. The floor of the field was marked out into 49 equal grids (each grid 10 cm×10 cm). At 30 minutes after administration of drug intraperitoneally into mice, each mouse was placed in the field and was monitored for behavior for 30 minutes. Observed items were as follows. Numbers of crossing lines of the grids by mouse were set as "movement score" and numbers of slipping the hindlimbs were set as "falling score". Each score was measured simultaneously. Ratio of both scores (falling score/movement score) is expressed as "falling index".

Drugs used were D-serine ethyl ester, 10, 50 and 250 mg/kg, respectively, D-cycloserine, 2, 10 and 50 mg/kg, respectively, and L-serine ethyl ester, 250 mg/kg. Physiological saline was used as control. Each drug and saline were administered intraperitoneally.
(Results)

Results of the movement score and the falling score (mean ± standard error) are shown in Table 2.

TABLE 2

Effect on drug induced ataxia mice

| Administration Component and Dose | Movement Score | Falling Index |
|---|---|---|
| D-Serine Ethyl ester (n = 6) | | |
| Physiological saline | 342 ± 98 | 0.87 ± 0.04 |
| 10 mg/kg | 386 ± 113 | 0.88 ± 0.09 |
| 50 mg/kg | 366 ± 96 | 0.66 ± 0.08* |
| 250 mg/kg | 412 ± 99 | 0.56 ± 0.06** |
| D-Cycloserine (n = 5) | | |
| Physiological saline | 220 ± 60 | 0.94 ± 0.08 |
| 2 mg/kg | 117 ± 54 | 0.80 ± 0.07 |

TABLE 2-continued

Effect on drug induced ataxia mice

| Administration Component and Dose | Movement Score | Falling Index |
|---|---|---|
| 10 mg/kg | 194 ± 71 | 0.69 ± 0.09* |
| 50 mg/kg | 286 ± 98 | 0.62 ± 0.04** |
| L-Serine Ethyl ester (n = 9) | | |
| Physiological saline | 184 ± 39 | 0.75 ± 0.05 |
| 250 mg/kg | 129 ± 27 | 0.80 ± 0.06 |

*Significant difference is observed in comparison with physiological saline ($p < 0.05$)
**Significant difference is observed in comparison with physiological saline ($p < 0.01$)

Significant decrease in the falling index, i.e. improved action on ataxia, was observed in the administration of D-serine ethyl ester 50 and 250 mg/kg and that of D-cycloserine, 10 and 50 mg/kg, as compared with the control group. However, since no significant effect on the movement score was observed in these groups, there may be no direct action on the locomotor activity.

No improved action on ataxia was observed even in the administration of L-serine ethyl ester 250 mg/kg. As a result, it was demonstrated that the improved action on ataxia was caused by D-form optically active isomer.

Example 2

Effect on Genetic Mutant Ataxia Mice

Genetic mutant ataxia mice, reeler mice (Heckroth, J. A. et al. J. Comp. Neurol., 279, 546–555, 1989 and Hamburgh, Dev. Biol., 8, 165–185, 1963) were purchased from Jackson Laboratory (Bar Harbor, Me., USA). Homozygotes were obtained by mating of heterozygote pairs. The homozygote male mice, 6–7 weeks old, were used for the experiments. It is well known that the numbers of the cerebellar Purkinje cells of the reeler mice are significantly decreased as compared with those of the normal mice, consequently such mice present ataxia due to cerebellar degeneration.

Experimental method for evaluation of ataxia was performed as same as in example 1. In the drug administered group, D-serine ethyl ester 250 mg/kg was administered intraperitoneally. For control group, physiological saline was administered.
(Results)

Results of the movement score and the falling index (mean ± standard error) are shown in Table 3. Improved effect on ataxia was observed by administration of D-serine ethyl ester 250 mg/kg as compared with the control group. No effect of D-serine ethyl ester was observed on the movement score.

TABLE 3

Effect on genetic mutant ataxia mice

| Administration Component and Dose | Movement Score | Falling Index |
|---|---|---|
| Physiological saline (n = 4) | 303 ± 79 | 0.43 ± 0.05 |
| D-Serine Ethyl ester 250 mg/kg (n = 4) | 232 ± 66 | 0.24 ± 0.05* |

*Significant difference is observed in comparison with physiological saline ($p < 0.05$)

Results of the above examples 1 and 2 indicate new knowledge that D-serine ethyl ester (which corresponds to prodrug of D-serine) or D-cycloserine improves ataxia caused by cerebellar degeneration, simultaneously showing possibility of these drugs as the remedy for spinocerebellar degeneration.

Industrial Applicability

According to the present invention, a remedy for spinocerebellar degeneration comprising one or more members selected from the group consisting of D-cycloserine, D-serine and D-serine ester as an active ingredient, a novel composition for treatment of spinocerebellar degeneration containing said remedy, a method for treatment of spinocerebellar degeneration using the same, and a use of the same for production of remedy for spinocerebellar degeneration are provided. The present invention is useful for improving symptoms mainly causing ataxia of spinocerebellar degeneration.

Especially, features in D-cycloserine have not been observed in the conventional remedy for spinocerebellar degeneration, consequently practical remedy having possibility for oral administration with long term action and less side effects can be provided.

What is claimed is:

1. A method for treating spinocerebellar degeneration in a patient comprising administering an effective amount of the D-cycloserine or a salt thereof to the patient with spinocerebellar degeneration.

* * * * *